United States Patent [19]

Yoshida et al.

[11] 4,260,411
[45] Apr. 7, 1981

[54] N'-PHENYL-N-METHYLUREA DERIVATIVES

[75] Inventors: Ryo Yoshida, Kawanishi; Ichiki Takemoto, Takarazuka; Seizo Sumida, Nishinomiya; Katsuzo Kamoshita, Osaka, all of Japan

[73] Assignee: Sumitomo Chemical Company, Limited, Osaka, Japan

[21] Appl. No.: 19,613

[22] Filed: Mar. 12, 1979

[30] Foreign Application Priority Data

Mar. 13, 1978 [JP] Japan ................................. 53-28897

[51] Int. Cl.³ ...................... A01N 47/30; C07C 127/19
[52] U.S. Cl. ................................. 71/88; 71/98; 71/105; 71/120; 260/340.5 R; 260/453 RW; 260/465 D; 424/282; 424/298; 424/304; 424/322; 564/49; 564/52
[58] Field of Search .... 260/453 RW, 553 A, 340.5 R, 260/465 D; 424/322, 282, 298, 304; 71/120, 88, 98, 105

[56] References Cited

U.S. PATENT DOCUMENTS

| | | | |
|---|---|---|---|
| 3,819,697 | 6/1974 | Cross | 260/553 A |
| 3,951,641 | 4/1976 | Janiak | 71/120 |
| 3,988,300 | 10/1976 | Cross | 260/553 A |
| 4,087,272 | 5/1978 | Rohe et al. | 71/120 |
| 4,123,256 | 10/1978 | Yoshida et al. | 71/105 |
| 4,129,436 | 12/1978 | Takemoto et al. | 71/120 |

FOREIGN PATENT DOCUMENTS 1516616 7/1978 United Kingdom .

OTHER PUBLICATIONS

Bernstein et al., J.A.C.S., vol. 70, pp. 2310–2315, (1948).
Pummerer et al., Berichte, vol. 55, pp. 3130–3133, (1922).

*Primary Examiner*—Dolph H. Torrence
*Attorney, Agent, or Firm*—Birch, Stewart, Kolasch and Birch

[57] ABSTRACT

A compound of the formula:

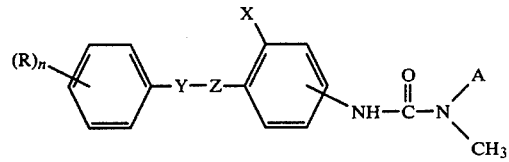

wherein A is a hydrogen atom, a methyl group or a methoxy group, Rs are same or different and each a halogen atom, a lower alkyl group, a lower alkoxy group, a lower alkylthio group, a trifluoromethyl group, a cyano group or a methylenedioxy group, X is a hydrogen atom or a halogen atom, Y is an oxygen atom or a sulfur atom, Z is a lower alkylene group and n is an integer of 0 to 3, provided that the substituted ureido group being present at the m- or p-position to the substituent represented by the symbol X and at the same time at the m- or p-position to the substituent represented by the symbol Z, which shows herbicidal and/or fungicidal activities and can be prepared, for instance, by reacting the corresponding phenyl isocyanate with a reagent of the formula:

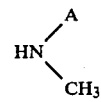

wherein A is as defined above.

18 Claims, No Drawings

N'-PHENYL-N-METHYLUREA DERIVATIVES

The present invention relates to N'-phenyl-N-methylurea derivatives, and their production and use.

The N'-phenyl-N-methylurea derivatives of the present invention are representable by the formula:

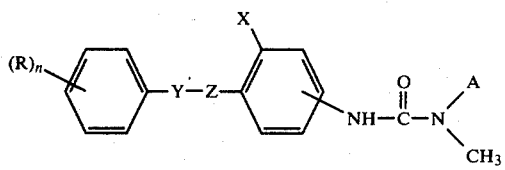

wherein A is a hydrogen atom, a methyl group or a methoxy group, Rs are same or different and each a halogen atom (preferably chlorine, bromine or fluorine), a lower alkyl group (e.g. methyl, ethyl, propyl, isopropyl, butyl), a lower alkoxy group (e.g. methoxy, ethoxy), a lower alkylthio group (e.g. methylthio), a trifluoromethyl group, a cyano group or a methylenedioxy group, X is a hydrogen atom or a halogen atom (preferably chlorine), Y is an oxygen atom or a sulfur atom, Z is a lower alkylene group (e.g. methylene, ethylene, propylene, trimethylene) and n is an integer of 0 to 3.

In the above formula (I), the substituted ureido group is present at the m- or p-position to the substituent represented by the symbol X and at the same time at the m-or p-position to the substituent represented by the symbol Z. The term "lower " is intended to mean a group having 1 to 5 carbon atoms. The preferred number of the carbon atoms is from 1 to 4 for "lower" alkyl and 1 or 2 for "lower" alkoxy.

Soybeans, peanuts, cotton, corn, wheat, rice, sugar beet and the like are crops of world-wide importance and, in the cultivation of these crops, chemical control of weeds is necessary to prevent reductions in the yield.

Among substituted urea derivatives, as is well known, there are compounds having a strong herbicidal activity, such as N'-4-chlorophenyl-N,N-dimethylurea (monuron) and N'-3,4-dichlorophenyl-N,N-dimethylurea (diuron). It is also well known that the herbicidal activity of these urea derivatives is due to the inhibition of photosynthesis. Photosynthesis is a physiological function peculiar to higher plants and does not take place in mammals. Accordingly, specific inhibitors of the photosynthetic process usually cause no significant harm to mammals but can be extremely effective in the extermination of higher plants. In fact, herbicidal photosynthesis inhibitors such as monuron, diuron, 5-bromo-3-sec-butyl-6-methyluracil (bromacil) and the like are all low in mammalian toxicity. However, they exert a herbicidal activity against all higher plants, i.e. crops and weeds alike, since photosynthesis is common to all of the higher plants. Most photosynthesis inhibitors are non-selective and damage crop plants.

A compound to be a selective herbicide should have both a strong herbicidal activity against weeds and a high level of selectivity to the intended crop. However, such selective herbicides are very difficult to find and can not easily be predicted by mere analogy and modification of known chemical structures. Therefore, a highly detailed study with trial and error is necessary to find such selective herbicides. Selective herbicidal activity requires a very specific chemical structure, and only a slight difference in the chemical structure can produce quite a large difference in the degrees and kind of selectivity.

It has now been found that the compounds of the formula (I) show a remarkable herbicidal activity with no phytotoxicity to rice plants in paddy field by soil treatment after transplantation. Besides, they can safely be used in upland field without phytotoxicity to rice plant, wheat, corn, soybeans, peanuts, cotton and sugar beet by pre-emergence application. The greatest characteristic of the present invention is that excellent foliar-applied herbicides which can safely be applied to said crop plants including wheat and soybeans can be provided. That is, when the compounds (I) are applied to soybean field as a foliar-applied agent, they can exterminate many weeds such as large crabgrass (*Digitaria sanguinalis*), cocklebur (*Xanthium pensylvanicum*), annual morningglory (*Ipomoea purpurea*), jimsonweed (*Datura stramonium*), sunflower (*Helianthus annuus*) and redroot pigweed (*Amaranthus retroflexus*), with little phytotoxicity to soybeans.

As described above, the compounds (I) are very useful as selective herbicides for crop lands and besides they can be used as excellent herbicides for non-crop land on account of their strong herbicidal activity.

In addition, it may be noted that the compounds (I) are effective in prevention and inhibition of plant diseases caused by various phytopathogenic fungi in crop plants and fruit trees such as powdery mildew in apples, pears, grapes, oranges, cucumbers, melons, wheat, etc., downy mildew in grapes, oranges, cucumbers, melons, etc., yellows in root crops and rust in wheats, beans, etc. They are particularly effective in prevention and inhibition of rust such as stripe rust in barleys and wheats caused by *Puccinia striiformis*, stem rust in barleys and wheats caused by *Puccinia graminis*, leaf rust in wheats caused by *Puccinia recondita*, crown rust in oats caused by *Puccinia coronata*, rust in soybeans caused by *Uromyces sojae* and rust in kidney beans caused by *Uromyces appendiculatus*. Compared with conventional fungicides, the compounds (I) are characteristic in having not only a preventive effect but also a curative effect.

Accordingly, the compounds (I) of the present invention are useful as herbicides and/or fungicides. Particularly when they are used in cultivation of paddy rice plant, upland rice plant, cotton, soybeans, corn, wheat, barley, etc., the simultaneous performance as a herbicide and a fungicide can be expected.

The compounds (I) are novel and can be produced, for instance, by the procedures as shown in the following scheme:

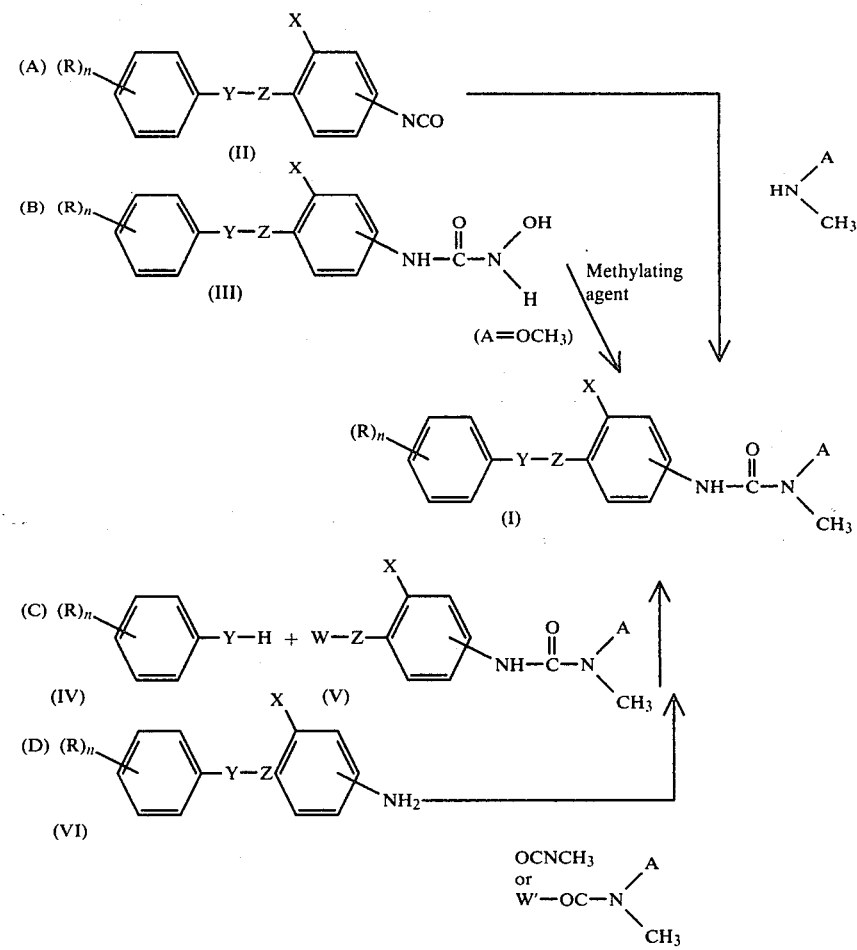

wherein W and W' are each a halogen atom (e.g. chlorine, bromine) and A, R, X, Y, Z and n are each as defined above.

Procedure (A)

The compound (I) is obtainable by reacting the phenyl isocyanate (II) with a reagent of the formula:

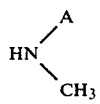 (1)

wherein A is as defined above.

The reaction may be carried out in an organic solvent (e.g. benzene, toluene, xylene, diethyl ether, tetrahydrofuran, dioxane, N,N-dimethylformamide, chloroform, carbon tetrachloride), water or mixture thereof. The regent (1) is used ordinarily in an amount of 1 to 3 mole, preferably in an amount of 1 to 1.5 mole, to 1 mole of the phenyl isocyanate (II). The reaction is effected usually at a temperature of 0° to 50° C. and comes to an end in 1 to 10 hours.

Procedure (B)

The compound (I) wherein A is methoxy is obtainable by reacting the hydroxyurea (III) with a methylating agent.

In the reaction, the methylating agent is normally employed in an amount of 2 to 6 mole, preferably in an amount of 2 to 4 mole, to the hydroxyurea (III). As the methylating agent, there may be used methyl iodide, dimethyl sulfate, diazomethane or the like. When dimethyl sulfate is used, for example, the reaction may be carried out in a solvent in the presence of an alkali. Examples of the alkali are sodium hydroxide and potassium hydroxide, and examples of the solvent are organic solvents (e.g. benzene, toluene, xylene, methanol, ethanol, isopropanol, diethyl ether, tetrahydrofuran, dioxane, methylene chloride), water and mixtures thereof. The existence of a phase transfer catalyst such as a quaternary ammonium salt (e.g. benzyltriethylammonium chloride, tetra-n-butylammonium bromide) in the reaction system is favorable for attaining a better result. The reaction is effected usually at a temperature of 0° to 100° C. and comes to an end in 1 to 10 hours.

Procedure (C)

The compound (I) is obtainable by reacting the (thio)phenol (IV) with the phenylalkyl halide (V).

In the reaction, the (thio)phenol (IV) and the phenylalkyl halide derivative (V) is usually employed in a molar proportion of 1–3:1, preferably of 1–1.5:1. the reaction may be carried out in an inert organic solvent (e.g. benzene, toluene, xylene, diethyl ether, tetrahydrofuran, dioxane, chloroform, carbon tetrachloride, methylene chloride, ethyl acetate, N,N-dimethylformamide) or water, or their mixture in the presence of a dehydrohalogneating agent (e.g. pyridine, triethylamine, sodium hydroxide, potassium hydroxide, sodium carbonate). The reaction is effected usually at a temperature of 0° to 120° C. and comes to an end in 0.5 to 10 hours.

Procedure (D)

The compound (I) is obtainable by reacting the aniline (VI) with a reagent selected from the group consisting of methyl isocyanate, N,N-dimethylcarbamyl halide and N-methoxy-N-methylcarbamyl halide.

In the reaction, the reagent is normally used in an amount of 1 to 3 mole, preferably in an amount of 1 to 1.5 mole, to 1 mole of the aniline (VI). The reaction may be carried out in an inert organic solvent (e.g. benzene, toluene, xylene, diethyl ether, tetrahydrofuran, dioxane, chloroform, carbon tetrachloride, methylene chloride, ethyl acetate, N,N-dimethylformamide), in case of the reagent being N,N-dimethylcarbamyl halide or N-methoxy-N-methylcarbamyl halide, in the presence of a dehydrohalogenating agent (e.g. pyridine, triethylamine, sodium hydroxide, potassium hydroxide, sodium carbonate). The reaction is effected usually at a temperature of 0° to 150° C. for 1 to 30 hours.

In the above procedures, the phenyl isocyanate (II) may be prepared by reacting the aniline (VI) with phosgene. In the reaction, phosgene is employed usually in an amount of 1 to 5 mole, favorably of 1 to 3 mole, to 1 mole of the aniline (VI). The reaction is normally carried out in an inert organic solvent (e.g. benzene, toluene, xylene, tetrahydrofuran, dioxane, chloroform, carbon tetrachloride, ethyl acetate) at room temperature (about 20° C.) to the reflux temperature of the solvent for a moment to 10 hours.

The hydroxyurea (III) can be obtained by reacting the phenyl isocyanate (II) with hydroxylamine. In the reaction, the phenyl isocyanate (II) and hydroxylamine are usually employed in a molar proportion of 1:1–3, preferably of 1:1–1.5. The reaction is ordinarily carried out in an organic solvent (e.g. benzene, toluene, xylene, diethyl ether, tetrahydrofuran, dioxane, chloroform, carbon tetrachloride) or water, or their mixture at a temperature of 0° to 50° C. for a moment to 30 hours. The aniline (VI) is obtainable by reduction of the corresponding nitrobenzene of the formula:

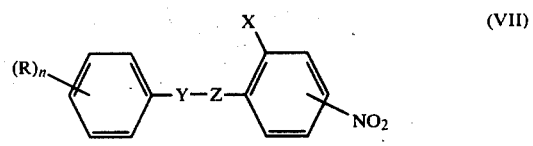

(VII)

wherein R, X, Y, Z and n are each as defined above, the latter being prepared by the method as disclosed in J.A.C.S., 70, 2310–2313 (1948).

Besides, the following patents disclose compounds, which are more or less structurally related to the compounds (I) of the invention, and their production: U.S. Pat. No. 4,123,256 issued Oct. 31, 1978; U.S. Pat. No. 4,129,436 issued Dec. 12, 1978; U.S. Pat. No. 4,144,049 issued Mar. 13, 1979.

Examples of the compound (I) of the invention are shown below.

| Compound No. | Chemical structure | Melting point or refractive index |
|---|---|---|
| 1 | (phenyl)–OCH$_2$–(phenyl)–NHC(=O)N(CH$_3$)(CH$_3$) | M.P., 128.5–130° C. |
| 2 | (phenyl)–OCH$_2$–(phenyl)–NHC(=O)N(CH$_3$)(OCH$_3$) | M.P., 72.5–73° C. |
| 3 | (3-Cl-phenyl)–OCH$_2$–(phenyl)–NHC(=O)N(CH$_3$)(CH$_3$) | M.P., 127–129° C. |
| 4 | (3-Cl-phenyl)–OCH$_2$–(phenyl)–NHC(=O)N(CH$_3$)(OCH$_3$) | M.P., 83–84° C. |
| 5 | (2-F-phenyl)–OCH$_2$–(phenyl)–NHC(=O)N(CH$_3$)(CH$_3$) | M.P., 113.5–115° C. |

-continued

| Compound No. | Chemical structure | Melting point or refractive index |
|---|---|---|
| 6 | 2-F-C₆H₄-OCH₂-C₆H₄-NHC(O)N(CH₃)(OCH₃) | M.P., 87–88° C. |
| 7 | 3-F-C₆H₄-OCH₂-C₆H₄-NHC(O)N(CH₃)₂ | M.P., 123–124.5° C. |
| 8 | 3-F-C₆H₄-OCH₂-C₆H₄-NHC(O)N(CH₃)(OCH₃) | M.P., 71–72.5° C. |
| 9 | 3-F₃C-C₆H₄-OCH₂-C₆H₄-NHC(O)N(CH₃)₂ | M.P., 111–112° C. |
| 10 | 3-F₃C-C₆H₄-OCH₂-C₆H₄-NHC(O)N(CH₃)(OCH₃) | M.P., 102–103° C. |
| 11 | 2-CH₃-C₆H₄-OCH₂-C₆H₄-NHC(O)N(CH₃)₂ | M.P., 131.5° C. |
| 12 | 2-CH₃-C₆H₄-OCH₂-C₆H₄-NHC(O)N(CH₃)(OCH₃) | M.P., 92° C. |
| 13 | 3-CH₃-C₆H₄-OCH₂-C₆H₄-NHC(O)N(CH₃)₂ | M.P., 128° C. |
| 14 | 3-CH₃-C₆H₄-OCH₂-C₆H₄-NHC(O)N(CH₃)(OCH₃) | M.P., 83° C. |
| 15 | 3-(i-Pr)-C₆H₄-OCH₂-C₆H₄-NHC(O)N(CH₃)₂ | M.P., 100.5–103° C. |
| 16 | 3-(i-Pr)-C₆H₄-OCH₂-C₆H₄-NHC(O)N(CH₃)(OCH₃) | M.P., 67–68° C. |

-continued

| Compound No. | Chemical structure | Melting point or refractive index |
|---|---|---|
| 17 | (CH₃)₃C-C₆H₄-OCH₂-C₆H₄-NHC(O)N(CH₃)₂ | M.P., 144.5–147° C. |
| 18 | (CH₃)₃C-C₆H₄-OCH₂-C₆H₄-NHC(O)N(CH₃)(OCH₃) | M.P., 85–86° C. |
| 19 | H₃CO-C₆H₄-OCH₂-C₆H₄-NHC(O)N(CH₃)₂ | M.P., 135–136.5° C. |
| 20 | H₃CO-C₆H₄-OCH₂-C₆H₄-NHC(O)N(CH₃)(OCH₃) | M.P., 76–79.5° C. |
| 21 | H₃CO-C₆H₄-OCH₂-C₆H₄-NHC(O)N(CH₃)₂ | M.P., 130.5–131° C. |
| 22 | H₃CO-C₆H₄-OCH₂-C₆H₄-NHC(O)N(CH₃)(OCH₃) | M.P., 77–80° C. |
| 23 | H₅C₂O-C₆H₄-OCH₂-C₆H₄-NHC(O)N(CH₃)₂ | M.P., 129–131° C. |
| 24 | H₅C₂O-C₆H₄-OCH₂-C₆H₄-NHC(O)N(CH₃)(OCH₃) | M.P., 70.5–71.5° C. |
| 25 | H₃CS-C₆H₄-OCH₂-C₆H₄-NHC(O)N(CH₃)₂ | M.P., 150.5–153.5° C. |
| 26 | H₃CS-C₆H₄-OCH₂-C₆H₄-NHC(O)N(CH₃)(OCH₃) | M.P., 68.5–69.5° C. |
| 27 | NC-C₆H₄-OCH₂-C₆H₄-NHC(O)N(CH₃)₂ | M.P., 134.5–136° C. |

-continued

| Compound No. | Chemical structure | Melting point or refractive index |
|---|---|---|
| 28 | NC—⟨C6H4⟩—OCH2—⟨C6H4⟩—NHC(O)N(CH3)(OCH3) | M.P., 117.5–119.5° C. |
| 29 | Cl,Cl—⟨C6H3⟩—OCH2—⟨C6H4⟩—NHC(O)N(CH3)2 | M.P., 143–145° C. |
| 30 | Cl,Cl—⟨C6H3⟩—OCH2—⟨C6H4⟩—NHC(O)N(CH3)(OCH3) | M.P., 102–104° C. |
| 31 | Cl,Cl—⟨C6H3⟩—OCH2—⟨C6H4⟩—NHC(O)N(CH3)2 | M.P., 150.5–152.5° C. |
| 32 | Cl,Cl—⟨C6H3⟩—OCH2—⟨C6H4⟩—NHC(O)N(CH3)(OCH3) | M.P., 105.5–106.5° C. |
| 33 | Cl,H3C—⟨C6H3⟩—OCH2—⟨C6H4⟩—NHC(O)N(CH3)2 | M.P., 135–135.5° C. |
| 34 | Cl,H3C—⟨C6H3⟩—OCH2—⟨C6H4⟩—NHC(O)N(CH3)(OCH3) | M.P., 104–105.5° C. |
| 35 | (methylenedioxyphenyl)—OCH2—⟨C6H4⟩—NHC(O)N(CH3)(OCH3) | M.P., 84–85.5° C. |
| 36 | F3C—⟨C6H4⟩—OCH2—⟨C6H3-Cl⟩—NHC(O)N(CH3)2 | M.P., 122–123.5° C. |
| 37 | F3C—⟨C6H4⟩—OCH2—⟨C6H3-Cl⟩—NHC(O)N(CH3)(OCH3) | M.P., 92.5–94° C. |

-continued

| Compound No. | Chemical structure | Melting point or refractive index |
| --- | --- | --- |
| 38 | Ph-SCH$_2$-C$_6$H$_4$-NHC(=O)N(CH$_3$)(CH$_3$) | M.P., 159–161° C. |
| 39 | Ph-SCH$_2$-C$_6$H$_4$-NHC(=O)N(CH$_3$)(OCH$_3$) | M.P., 106.5–107° C. |
| 40 | 3-F$_3$C-C$_6$H$_4$-O-CH(CH$_3$)-C$_6$H$_4$-NHC(=O)N(CH$_3$)(OCH$_3$) | M.P., 112–113.5° C. |
| 41 | 2,6-Cl$_2$-4-CH$_3$-C$_6$H$_2$-OCH$_2$-C$_6$H$_4$-NHC(=O)N(OCH$_3$)(CH$_3$) | M.P., 93–94° C. |
| 42 | 3-Cl-C$_6$H$_4$-OCH$_2$-C$_6$H$_4$-NHC(=O)N(CH$_3$)(CH$_3$) | M.P., 109–110° C. |
| 43 | 3-Cl-C$_6$H$_4$-OCH$_2$-C$_6$H$_4$-NHC(=O)N(CH$_3$)(OCH$_3$) | M.P., 68–70° C. |
| 44 | 3-CH$_3$O-C$_6$H$_4$-OCH$_2$-C$_6$H$_4$-NHC(=O)N(CH$_3$)(CH$_3$) | M.P., 85–86° C. |
| 45 | 3-CH$_3$O-C$_6$H$_4$-OCH$_2$-C$_6$H$_4$-NHC(=O)N(CH$_3$)(OCH$_3$) | M.P., 76–79° C. |
| 46 | 3-CH$_3$-C$_6$H$_4$-OCH$_2$-C$_6$H$_4$-NHC(=O)N(CH$_3$)(CH$_3$) | M.P., 135–136° C. |
| 47 | 3-CH$_3$-C$_6$H$_4$-OCH$_2$-C$_6$H$_4$-NHC(=O)N(CH$_3$)(OCH$_3$) | M.P., 101–102° C. |
| 48 | 2-Br-C$_6$H$_4$-OCH$_2$-C$_6$H$_4$-NHC(=O)N(CH$_3$)(CH$_3$) | M.P., 106–108° C. |
| 49 | 2-Br-C$_6$H$_4$-OCH$_2$-C$_6$H$_4$-NHC(=O)N(CH$_3$)(OCH$_3$) | $n_D^{20}$ 1.5782 |
| 50 | 2-CH(CH$_3$)$_2$-C$_6$H$_4$-OCH$_2$-C$_6$H$_4$-NHC(=O)N(CH$_3$)(CH$_3$) | M.P., 103–104° C. |

-continued

| Compound No. | Chemical structure | Melting point or refractive index |
|---|---|---|
| 51 | 2-(CH(CH$_3$)$_2$)-C$_6$H$_4$-OCH$_2$-C$_6$H$_4$-NHC(=O)N(CH$_3$)(OCH$_3$) | $n_D^{20}$ 1.5569 |
| 52 | 2-F-C$_6$H$_4$-OCH$_2$-C$_6$H$_4$-NHC(=O)N(CH$_3$)$_2$ | M.P., 142.5–143° C. |
| 53 | 2-F-C$_6$H$_4$-OCH$_2$-C$_6$H$_4$-NHC(=O)N(CH$_3$)(OCH$_3$) | M.P., 117–118° C. |
| 54 | 2-Cl-3,5-(H$_3$C)$_2$-C$_6$H$_2$-OCH$_2$-C$_6$H$_4$-NHC(=O)N(CH$_3$)$_2$ | M.P., 93–94° C. |
| 55 | 2,5-(CH$_3$)$_2$-C$_6$H$_3$-OCH$_2$-C$_6$H$_4$-NHC(=O)N(CH$_3$)(OCH$_3$) | M.P., 144–146° C. |
| 56 | 2-CH$_3$-C$_6$H$_4$-OCH$_2$-C$_6$H$_4$-NHC(=O)N(CH$_3$)$_2$ | M.P., 171–177° C. |
| 57 | 2-Cl-C$_6$H$_4$-OCH$_2$-C$_6$H$_4$-NHC(=O)N(CH$_3$)$_2$ | M.P., 136–138° C. |
| 58 | C$_6$H$_5$-OCH$_2$CH$_2$-C$_6$H$_4$-NHC(=O)N(CH$_3$)$_2$ | M.P., 113–115° C. |
| 59 | C$_6$H$_5$-OCH$_2$CH$_2$-C$_6$H$_4$-NHC(=O)N(CH$_3$)(OCH$_3$) | $n_D^{19}$ 1.661 |
| 60 | 4-(H$_3$C)$_3$C-C$_6$H$_4$-OCH$_2$CH$_2$-C$_6$H$_4$-NHC(=O)N(CH$_3$)$_2$ | M.P., 112–118° C. |
| 61 | 4-(H$_3$C)$_3$C-C$_6$H$_4$-OCH$_2$CH$_2$-C$_6$H$_4$-NHC(=O)N(CH$_3$)(OCH$_3$) | $n_D^{23}$ 1.6535 |
| 62 | 4-H$_3$C-C$_6$H$_4$-OCH$_2$-(3-Cl-C$_6$H$_3$)-NHC(=O)N(CH$_3$)$_2$ | M.P., 138–139° C. |
| 63 | 4-H$_3$C-C$_6$H$_4$-OCH$_2$-(3-Cl-C$_6$H$_3$)-NHC(=O)N(CH$_3$)(OCH$_3$) | M.P., 103–107° C. |
| 64 | 3-Cl-C$_6$H$_4$-OCH$_2$-(3-Cl-C$_6$H$_3$)-NHC(=O)N(CH$_3$)$_2$ | M.P., 132–133° C. |

-continued

| Compound No. | Chemical structure | Melting point or refractive index |
|---|---|---|
| 65 | 3-Cl-C6H4-OCH2-(3-Cl,4-)C6H3-NHC(O)N(CH3)(OCH3) | M.P., 103–104° C. |
| 66 | C6H5-OCH2-(3-Cl,4-)C6H3-NHC(O)N(CH3)(CH3) | M.P., 152–153° C. |
| 67 | C6H5-OCH2-(3-Cl,4-)C6H3-NHC(O)N(CH3)(OCH3) | M.P., 100–101° C. |
| 68 | 4-(H3C)3C-C6H4-SCH(CH3)CH2-C6H4-NHC(O)N(CH3)(CH3) | $n_D^{20.5}$ 1.5746 |
| 69 | 4-(H3C)3C-C6H4-SCH(CH3)CH2-C6H4-NHC(O)N(CH3)(OCH3) | $n_D^{20.5}$ 1.5716 |
| 70 | C6H5-OCH2-C6H4-NHC(O)N(CH3)(CH3) | M.P., 138–139° C. |
| 71 | C6H5-OCH2-C6H4-NHC(O)N(CH3)(OCH3) | M.P., 144–115° C. |
| 72 | 2-CH3O-C6H4-OCH2-C6H4-NHC(O)N(CH3)(CH3) | M.P., 128–130° C. |
| 73 | 2-CH3O-C6H4-OCH2-C6H4-NHC(O)N(CH3)(OCH3) | M.P., 112–113° C. |
| 74 | 2-CH3O-C6H4-OCH2-C6H4-NHC(O)N(CH3)(H) | M.P., 167–168° C. |
| 75 | (4-Cl,3-CH3)C6H3-OCH2-C6H4-NHC(O)N(CH3)(CH3) | M.P., 118.5–119° C. |
| 76 | (4-Cl,3-CH3)C6H3-OCH2-C6H4-NHC(O)N(CH3)(OCH3) | M.P., 116.5–117° C. |
| 77 | (2-Br,3,5-(CH3)2)C6H2-OCH2-C6H4-NHC(O)N(CH3)(CH3) | M.P., 132.5–133° C. |
| 78 | (2-Br,3,5-(CH3)2)C6H2-OCH2-C6H4-NHC(O)N(CH3)(OCH3) | M.P., 89.5–90° C. |

-continued

| Compound No. | Chemical structure | Melting point or refractive index |
|---|---|---|
| 79 | H3C-[benzene(3,5-diCH3)]-OCH2-[benzene]-NHC(=O)N(CH3)(CH3) | M.P., 149.5–150° C. |
| 80 | H3C-[benzene(3,5-diCH3)]-OCH2-[benzene]-NHC(=O)N(CH3)(OCH3) | M.P., 134.5–135° C. |
| 81 | [phenyl]-OCH(CH3)CH2-[benzene(m)]-NHC(=O)N(CH3)(CH3) | $n_D^{24.0}$ 1.6601 |
| 82 | [phenyl]-OCH(CH3)CH2-[benzene(m)]-NHC(=O)N(CH3)(OCH3) | $n_D^{21.0}$ 1.5444 |
| 83 | CH3-[benzene]-OCH2CH2CH2CH2CH2-[benzene(m)]-NHC(=O)N(CH3)(CH3) | M.P., 83–84.5° C. |
| 84 | CH3-[benzene]-OCH2CH2CH2CH2CH2-[benzene(m)]-NHC(=O)N(CH3)(OCH3) | M.P., 97.0–97.5° C. |
| 85 | Cl,Cl,Cl-[benzene]-OCH2-[benzene]-NHC(=O)N(OCH3)(CH3) | M.P., 136.5–138° C. |
| 86 | H3C,Cl,Cl-[benzene]-OCH2-[benzene]-NHC(=O)N(OCH3)(CH3) | M.P., 121–128° C. |
| 87 | [benzene(o-F)]-OCH2-[benzene(m)]-NHC(=O)N(OCH3)(CH3) | M.P., 87–88° C. |

The production of the compound (I) according to the invention are illustratively shown by the following Examples.

EXAMPLE 1 (PROCEDURE (A))

To a solution of M-(m-methylphenoxymethyl)phenyl isocyanate (23.9 g) in benzene (100 ml) was added dropwise a solution of N,O-dimethylhydroxylamine (7.3 g) in benzene (50 ml) at a temperature below 30° C. The reaction mixture was allowed to stand at room temperature for 2 hours, and the solvent was removed under reduced pressure. The residue was recrystallized from methanol to obtain 23.3 g of N'-m-(m-methylphenoxymethyl)phenyl-N-methoxy-N-methylurea (Compound No. 14) as white needles. M.P., 83° C.

Elementary analysis: Calcd. for $C_{17}H_{20}N_2O_3$: C, 67.98%; H, 6.71%; N, 9.33%. Found: C, 67.81%; H, 6.85%; N, 9.26%.

NMRδCDCl3: 2.30 (s, 3H), 3.11 (s, 3H), 3.68 (s, 3H), 4.94 (s, 2H), 6.50–7.40 (8H), 7.65 (s, 1H).

EXAMPLE 2 (PROCEDURE (B))

To a solution of N'-m-m(m-methoxyphenoxymethyl)-phenyl-N-hydroxyurea (30.0 g) in a benzene/methanol (1:1) mixture (150 ml), there were alternatively added portionwise dimethyl sulfate (29 ml) and an aqueous solution of sodium hydroxide (10N, 80 ml) at a temperature below 30° C. After stirring at room temperature for 2 hours, the reaction solution was diluted with water and extracted with benzene. After washing the benzene layer with water, the solvent was removed under reduced pressure and the oily residue was purified by column chromatography on silica gel (100–120 mesh) using a tetrahydrofuran/benzene (1:3) mixture as an eluent. The obtained crystals were recrystallized from ethanol to obtain 18.3 g of N'-m-(m-methoxyphenoxymethyl)- phenyl-N-methoxy-N-methylurea (Compound No. 20) as white crystals. M.P., 76°–79.5° C.

Elementaly analysis: Calcd. for $C_{17}H_{20}N_2O_4$: C, 64.53%; H, 6.38%; N, 8.86%. Found: C, 64.60%; H, 6.45%; N, 8.74%.

NMR$\delta$CDCl$_3$: 3.13 (s, 3H), 3.71 (s, 6H), 4.95 (s, 2H), 6.46–7.50 (8H), 7.58 (s, 1H).

EXAMPLE 3 (PROCEDURE (C))

To a solution of 3,4-dichlorophenol (16.3 g) in ethanol (100 ml) was added 50% aqueous potassium hydroxide solution (12.3 g). To the mixture, a solution of N'-m-chloromethylphenyl-N,N-dimethylurea (21.3 g) in ethanol (50 ml) was added dropwise at 70° to 80° C. Thereafter, the reaction mixture was heated under reflux for 2 hours and allowed to stand at room temperature. The mixture was diluted with water and extracted with benzene. After washing the benzene layer with water, the solvent was removed under reduced pressure. The residue was recrystallized from ethanol to obtain 27.3 g of N'-m-(3,4-dichlorophenoxymethyl)phenyl-N,N-dimethylurea (Compound No. 29) as white crystals. M.P., 143°–145° C.

Elementary analysis: Calcd. for $C_{16}H_{16}O_2N_2Cl_2$:C, 56.56%; H, 4.76%; N, 8.26%; Cl, 20.90%. Found: C, 56.46%; H, 4.90%; N, 8.41%; Cl, 20.77%.

NMR$\delta$CDCl$_3$: 2.94 (s, 6H), 4.93 (s, 2H), 6.60–7.60 (7H), 7.92(s, 1H).

EXAMPLE 4 (PROCEDURE (A))

Dried dimethylamine was bubbled into a solution of 4-(3-methylphenoxymethyl)phenyl isocyanate (11.3 g) in benzene (50 ml) at a temperature below 30° C. for 10 minutes. After stirring at room temperature for 1 hour, the solvent was removed under reduced pressure, and the residue was recrystallized from ethanol to obtain 5.5 g of N'-4-(3-methylphenoxymethyl)phenyl-N,N-dimethylurea (Compound No. 46) as white needles. M.P., 135°–136° C.

Elementary analysis: Calcd. for $C_{17}H_{20}O_2N_2$: C, 71.67%; H, 7.08%; N, 9.85%. Found: C,71.65%; H, 7.08%; N, 9.85%.

NMR$\delta$CDCl$_3$: 2.25 (s, 3H), 2.90 (s, 6H), 4.85 (s, 2H), 6.30 (broad s, 1H), 7.25–6.40 (8H).

EXAMPLE 5 (PROCEDURE (B))

To a mixture of N'-4-(3-methoxyphenoxymethyl)-phenyl-N-hydroxyurea (5.76 g, 0.02 mole) and dimethyl sulfate (5.54 g, 0.044 mole) in toluene (60 ml) was added tetra-n-butylammonium bromide (0.065 g, 0.0002 mole). To the mixture, an aqueous solution of sodium hydroxide (10 N, 4.4 ml, 0.044 mole) was added dropwise at 20° to 22° C. over period of 30 minutes while stirring. After stirring at 20° to 22° C. for 3 hours, an organic layer was washed with water, dried over sodium sulfate and concentrated. The residue was dried in vacuo to obtain 5.74 g of white crystal which was identified by elementary analysis and NMR spectra as N'-4-(3-methoxyphenoxymethyl)phenyl-N-methyl-N-methoxyurea (Compound No. 45). M.P., 76°–79° C.

Elementary analysis: Calcd. for $C_{17}H_{20}O_4N_2$: C, 64.54%; H, 6.37%; N, 8.86%. Found: C, 64.39%; H, 6.32%; N, 8.81%.

NMR$\delta$CDCl$_3$: 3.00(s, 3H), 3.58 (s, 3H), 3.60 (s, 3H), 4.78 (s, 2H), 6.00–7.40 (8H), 7.54 (1H).

EXAMPLE 6 (PROCEDURE (C))

To a solution of phenol (9.4 g) in ethanol (100 ml) was added 50% aqueous potassium hydroxide solution (12.3 g). To the mixture, a solution of N'-4-chloromethylphenyl-N,N-dimethylurea (21.3 g) in ethanol (50 ml) was added dropwise at 70° to 80° C. Thereafter, the reaction mixture was heated under reflux for 2 hours and allowed to stand at room temperature. The mixture was diluted with water and extracted with benzene. After washing the benzene layer with water, the solvent was removed. The residue was recrystallized from ethanol to obtain 8.8 g of N'-4-(phenoxymethyl)phenyl-N,N-dimethylurea (Compound No. 70) as white needles. M.P., 138°–139° C.

Elementary analysis: Calcd. for $C_{16}H_{18}O_2N_2$: C, 70.95%; H, 6.69%; N, 10.35%. Found: C, 70.94%; H, 6.69%; N, 10.38%.

NMR$\delta$CDCl$_3$: 2.92 (s, 6H), 4.90 (s, 2H), 6.70–8.00 (10H).

EXAMPLE 7 (PROCEDURE (D))

To a solution of 3-chlorophenyl-4-aminobenzyl ether (8.2 g) in dry pyridine (25 ml) was added dropwise dimethylcarbamoyl chloride (3.8 g) at 25° to 50° C. while stirring. After stirring overnight, the reaction mixture was poured into ice water. After the mixture was allowed to stand for 2 hours, the organic layer was separated from the aqueous layer. The aqueous layer was extracted with chloroform and the extract was combined with the organic layer. The combined organic layer was washed with water, and the solvent was removed under reduced pressure. The residue was recrystallized from ethanol to obtain 4.1 g of N'-4-(3-chlorophenoxymethyl)phenyl-N,N-dimethylurea (Compound No. 42) as white crystals. M.P., 109°–110° C.

Elementary analysis: Calcd. for $C_{16}H_{17}O_2N_2Cl$: C, 62.95%; H, 5.61%; N, 9.18%; Cl, 11.61%. Found: C, 62.92%; H, 5.60%; N, 9.19%; Cl, 11.63%.

NMR$\delta$CDCl$_3$: 2.90 (s, 6H), 4.80 (s, 2H), 6.20–6.20 (9H).

EXAMPLE 8 (Procedure (A))

To a solution of p-(o-methoxyphenoxymethyl)phenyl isocyanate (22.5 g) in benzene (100 ml) was added dropwise at a temperature below 30° C. a solution of monomethylamine (37.3 g) in benzene (100 ml). After the reaction mixture was allowed to stand at room temperature for 1 hour, the solvent was removed under reduced pressure. The residue was recrystallized from ethanol to obtain 17.3 g of N'-m-(o-methoxyphenoxymethyl)phenyl-N-methylurea (Compound No. 74) as white needles. M.P., 167°–168° C.

Elementary analysis: Calcd. for $C_{17}H_{20}N_2O_4$: C, 64.53%; H, 6.38%; N, 8.86%. Found: C, 64.57%; H, 6.34%; N, 8.89%.

NMRδCDCl₃-DMSOd₆: 2.75 (d, 3H), 3.82 (s, 3H), 5.00 (s, 2H), 5.81 (m, 1H), 6.91 (s, 4H), 7.36 (m, 4H), 8.22 (s, 1H).

EXAMPLE 9 (Preparation of the phenyl isocyanate (II))

A solution of 4-phenoxymethylaniline (10 g) in toluene (100 ml) was added dropwise to a solution of phosgene (20 g) in toluene (100 ml) at 10° to 20° C. The mixture was gradually heated and refluxed for 30 minutes. Thereafter, the reaction mixture was cooled to room temperature, and the solvent was evaporated under reduced pressure to give 7 g of 4-phenoxymethylphenyl isocyanate. M.P., 56°-57° C.

Elementary analysis: Calcd. for C₁₄H₁₁NO₂: C, 74.64%; H, 4.93%; N, 6.22%. Found: C, 74.53%; H, 4.86%; N, 6.35%.

NMRδCDCl₃: 4.92 (s, 2H), 6.80-7.50 (9H).

In the same manner as above, the following phenyl isocyanate was obtained:

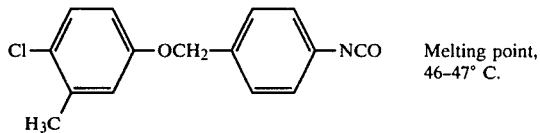

Melting point, 46-47° C.

EXAMPLE 10 (Preparation of the hydroxyurea (III))

An aqueous solution of sodium hydroxide (10N, 9.7 ml) was added dropwise to a solution of hydroxylamine hydrochloride (6.7 g) in water (10 ml) while cooling with ice. To the mixture, a solution of 4-(3-methyl-4-chlorophenoxymethyl)phenyl isocyanate (4.6 g) in toluene (50 ml) was slowly added at a temperature below 10° C. The reaction mixture was allowed to stand overnight at room temperature. The mixture was then extracted with ethyl acetate, and the ethyl acetate layer was washed with water and dried over sodium sulfate. The solvent was removed under reduced pressure to obtain 4.1 g of N'-4-(3-methyl-4-chlorophenoxymethyl)phenyl-N-hydroxyurea. M.P., 155°-156° C.

Elementary analysis: Calcd. for C₁₅H₁₅O₃N₂Cl: C, 58.72%; H, 4.94%; N, 9.13%; Cl, 11.56%. Found: C, 58.69%; H, 4.85%; N, 9.01%; Cl, 11.55%.

NMRδCDCl₃: 2.30 (s, 3H), 5.00 (s, 2H), 6.70-7.80 (7H), 8.75 (s, 1H), 8.80 (s, 1H), 8.90 (s, 1H).

In the same manner as above, the following hydroxyurea was obtained:

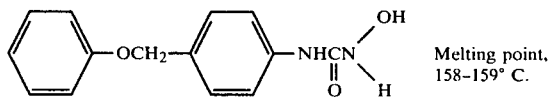

Melting point, 158-159° C.

In the practical usage of the compounds (I), they may be applied as such or in any preparation form such as wettable powders, emulsifiable concentrates, water dispersible liquids, granules, fine granules or dusts.

In producing such preparation form, a solid or liquid carrier or diluent may be used. As for the solid carrier or diluent, there may be given mineral powders (e.g. kaolin, bentonite, clay, montmorillonite, talc, diatomaceous earth, mica, vermiculite, gypsum, calcium carbonate, apatite), vegetable powders ((e.g. soybean powder, wheat flour, wooden powder, tobacco powder, starch, crystalline cellulose), high molecular weight compounds (e.g. petroleum resin), alumina, wax and the like.

As for the liquid carrier or diluent, there may be given alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, quaternary ammonium salts and the like. But, the surface active agent is not of course limited to these compounds. And, if necessary, gelatin, casein, sodium alginate, starch, agar, polyvinyl alcohol or the like may be used as an auxiliary agent.

In the herbicidal and/or fungicidal composition of the invention, the content of the compound (I) as an active ingredient may be from 1 to 100% by weight, preferably from 5 to 80% by weight.

Practical embodiments of the herbicidal and/or fungicidal composition according to the invention are illustratively shown in the following examples wherein parts and % are by weight.

PREPARATION EXAMPLE 1

Eighty parts of Compound No. 4, 5 parts of polyoxyethylene alkylaryl ether and 15 parts of synthetic silicon oxide hydrate are well mixed while being powdered to obtain a wettable powder.

PREPARATION EXAMPLE 2

Thirty parts of Compound No. 10, 7 parts of polyoxyethylene alkylaryl ether, 3 parts of alkylaryl sulfonate and 60 parts of xylene are well mixed to obtain an emulsifiable concentrate.

PREPARATION EXAMPLE 3

One part of Compound No. 20, 1 part of white carbon, 5 parts of ligninsulfonate and 93 parts of clay are well mixed while being powdered. The mixture is then well kneaded with water, granulated and dried to obtain a granule.

PREPARATION EXAMPLE 4

Fourty parts of bentonite, 5 parts of ligninsulfonate and 55 parts of clay are well mixed while being powdered. The mixture is then well kneaded with water, granulated and dried to obtain a granule containing no active ingredient. The granule is then impregnated with 5 parts of Compound No. 8 to obtain a granule.

PREPARATION EXAMPLE 5

Three parts of Compound No. 30, 0.5 part of isopropyl phosphate, 66.5 parts of clay and 30 parts of talc are well mixed while being powdered to obtain a dust.

PREPARATION EXAMPLE 6

Two parts of Compound No. 58, 88 parts of clay and 10 parts of talc are well mixed while being powdered to obtain a dust containing 2% of the active ingredient.

PREPARATION EXAMPLE 7

Three parts of Compound No. 82, 67 parts of clay and 30 parts of talc are well mixed while being powdered to obtain a dust containing 3% of the active ingredient.

The compounds (I) of the invention may be used together with other herbicides to improve their activity as herbicides, and in some cases, a synergistic effect can be expected. As the other herbicides, there may be given phenoxy series herbicides such as 2,4-dichlorophenoxyacetic acid and 2,4-dichlorophenoxybutyric acid (including esters and salts thereof); diphenyl ether series herbicides such as 2,4-dichlorophenyl-4'-nitrophenyl ether, 2,4-dichlorophenyl-4'-nitro-3'-methoxyphenyl ether, 2,4-dichlorophenyl-3'-methoxycarbonyl-4'-nitrophenyl ether and 2-chloro-4-trifluoromethylphenyl-3'-hydroxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine and 2-methylthio-4,6-bisethylamino-1,3,5-triazine; urea series herbicides such as 3-(3,4-dichlorophenyl)-1,1-dimethylurea, 3-(3,4-dichlorophenyl)-1-methoxy-1-methylurea, 3-[4-(4-chlorophenoxy)phenyl]-1,1-dimethylurea and 3-($\alpha,\alpha,\alpha$-trifluoro-m-tolyl)-1,1-dimethylurea; carbamate series herbicides such as isopropyl-N-(3-chloro-phenyl)carbamate, methyl-N-(3,4-dichlorophenyl)carbamate and 4-chloro-2-butynyl-m-chlorocarbanilate; thiolcarbamate series herbicides such as S-(4-chlorobenzyl)-N,N-diethylthiolcarbamate and S-ethyl dipropylthiolcarbamate; acid anilide series herbicides such as 3,4-dichloropropionanilide, N-methoxymethyl-2,6-diethyl-2-chloroacetanilide and 2-chloro-2',6'-diethyl-N-(butoxymethyl)acetanilide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; organic phosphorus series herbicides such as N-(phosphonomethyl)glycine, O-methyl-O-(2-nitro-4-methylphenyl)-N-isopropylphosphoroamidothioate and O-ethyl-O-(2-nitro-5-methylphenyl)-N-sec-butylphosphoroamidothioate; toluidine series herbicides such as $\alpha,\alpha,\alpha$-trifluoro-2,6-dinitro-N,N-dipropyl-p-toluidine; N-sec-butyl-4-tert-butyl-2,6-dinitroaniline; 3,5-dinitro-$N^4,N^4$-dipropylsulfanylamide; 5-tert-butyl-3-(2,4-dichloro-5-isopropoxyphenyl)-1,3,4-oxadiazolin-2-one; 3-isopropyl-1H-2,1,3-benzothiadiazine(4)-3H-one-2,2-dioxide (including salts thereof); 2-($\beta$-naphthoxy)-propionanilide; 2-($\alpha$-naphthoxy)-N,N-diethylpropionanilide; 3-amino-2,5-dichlorobenzoic acid; 2-sec-butyl-4,6-dinitrophenol; N-1-naphthylphthalamic acid; 2-[1-(N-allyloxyamino)-butylidene]-5,5-dimethyl-4-methoxycarbonyl-cyclohexane-1,3-dione (including salts thereof); 2-[4-(3,5-dichloropyridine-2-hydroxy)phenoxy]propionic acid (including salts thereof); 2-[4-(2,4-dichlorophenoxy)phenoxy]propionic acid (including esters and salts thereof) and the like. But, the herbicides are not of course limited to these examples.

The compounds (I) may be also applied together with common fungicides, microbial insecticides, pyrethroid series insecticides, other insecticides, plant growth regulators or fertilizers.

Examples of the fungicides which may be used in combination with the compounds (I) are as follows: N-(3,5-dichlorophenyl)-1,2-dimethylcyclopropane-1,2-dicarboximide, S-n-butyl-S-p-t-butylbenzyl-N-3-pyridyldithiocarbonimidate, O,O-dimethyl-O-2,6-dichloro-4-methylphenyl phosphorothioate, methyl-N-benzimidazol-2-yl-N-(butylcarbamoyl) carbamate, N-trichloromethylthio-4-cyclohexene-1,2-dicarboximide, cis-N-(1,1,2,2-tetrachloroethylthio)-4-cyclohexane-1,2-dicarboximide, polyoxin, streptomycin, zinc ethylenebisdithiocarbamate, zinc dimethylthiocarbamate, manganese ethylenebisdithiocarbamate, bis (dimethylthiocarbamoyl) disulfide, tetrachloroisophthalonitrile, 8-hydroxyquinoline, dodecylguanidine acetate, 5,6-dihydro-2-methyl-1,4-oxathiin-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis (3-methoxycarbonyl-2-thioureido) benzene, etc. Examples of the insecticides which may be employed together with the compounds (I) of the invention are O,O-dimethyl-O-(4-nitro-m-tolyl) phosphorothioate, O-p-cyanophenol-O,O-dimethylphosphorothioate, O-p-cyanophenyl-O-ethylphenylphosphonothioate, O,O-dimethyl-S-(N-methylcarbamoylmethyl)phosphorodithioate, 2-methoxy-4H-1,3,2-benzodioxaphosphorin-2-sulfide, O,O-dimethyl-S-(1-ethoxycarbonyl-1-phenylmethyl)phosphorodithioate, 1-cyano-3-phenoxybenzyl-2-(4-chlorophenyl)-isovaleate, 3-phenoxybenzyl2,2-dimethyl-3-(2,2-dichlorovinyl)cyclopropanecarboxylate, 3-phenoxybenzylchrysanthemate, etc.

The dosage rate of the compounds (I) as a herbicide depends upon their kinds, the sorts of cultivated plants, the application method, the weather, etc. Generally, however, the dosage rate is from 2 to 200 grams, preferably from 5 to 50 grams, of the active ingredient per are.

The dosage rate of the compounds (I) as a fungicide also depends upon their preparation methods, kinds of diseases, sorts of cultivated plants, time of application, etc. In general, the active ingredient may be applied in an amount of from 0.2 to 50 grams per are, and the concentration thereof is preferably from 0.001 to 1.0% by weight.

The application of the compounds (I) as herbicides and/or fungicides will be illustrated in the following Examples wherein the phytotoxicity to cultivated plant and the herbicidal activity on weeds were evaluated as follows: the aereal parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of plant.

| Rating value | Fresh weight (percentage to untreated plot) (%) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

MCP: 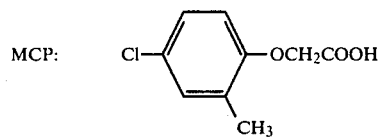

Chloroxuron: 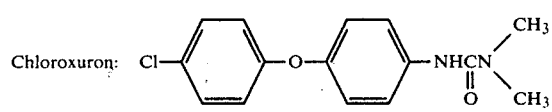

Bentazon: 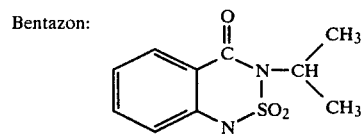

Fluometuron: 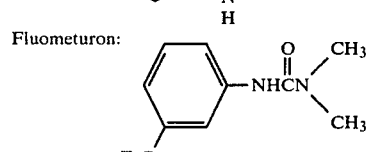

Atrazine: 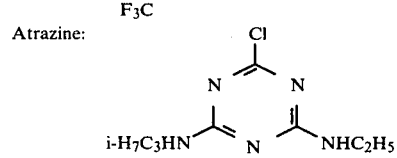

Diuron: 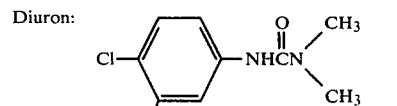

Chloramben: 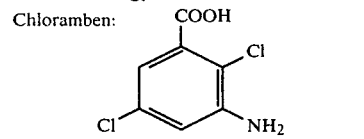

N'-(m-Benzyloxyphenyl)-N,N-dimethylurea
(U.S. Pat. No. 3,819,697):

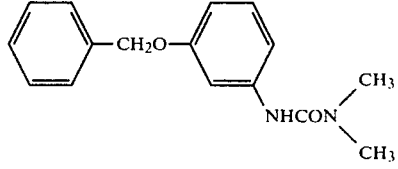

EXAMPLE 11 (Paddy rice test)

Wagner's pots (1/5000 are) were each filled with 1.5 kg of paddy field soil containing the seeds of weeds and kept under flooded conditions. The seedlings of rice plant at a 3-leaf stage were transplanted thereto, and after the seeds of barnyard grass were sowed therein, the seedlings were grown for 15 days in a green-house. Thereafter, the required amount of the wettable powder of each test compound was diluted with water and applied to the soil under flooded conditions. Twenty-five days after the application, the evaluation of herbicidal activity and phytotoxicity was made on the rice plants and barnyard grass as well as broadleaved weeds (e.g. pickerel weed (*Monochoria vaginalis*), false pimpernel (*Linderna pyxidaria*), toothcup (*Rotala indica* Koehne)) and nutsedge sp. (*Cyperus difformis*). The results are shown in Table 1.

TABLE 1

| Compound No. | Dosage (weight of active ingredient, g/are) | Evaluation of crop damage and herbicidal activity | | | |
|---|---|---|---|---|---|
| | | Rice plant | Barnyard grass | Broadleaved weed | Nutsedge sp. |
| 1 | 20 | 0 | 4 | 5 | 5 |
| | 10 | 0 | 4 | 5 | 5 |
| 2 | 20 | 0 | 4 | 5 | 5 |
| | 10 | 0 | 4 | 5 | 5 |
| 3 | 20 | 0 | 4 | 5 | 5 |
| | 10 | 0 | 4 | 5 | 5 |
| 4 | 20 | 0 | 5 | 5 | 5 |
| | 10 | 0 | 5 | 5 | 5 |
| 5 | 20 | 0 | 5 | 5 | 5 |
| | 10 | 0 | 4 | 5 | 5 |
| 6 | 20 | 0 | 5 | 5 | 5 |
| | 10 | 0 | 5 | 5 | 5 |
| 7 | 20 | 0 | 5 | 5 | 5 |
| | 10 | 0 | 5 | 5 | 5 |
| 8 | 20 | 0 | 5 | 5 | 5 |
| | 10 | 0 | 5 | 5 | 5 |
| 9 | 20 | 0 | 5 | 5 | 5 |
| | 10 | 0 | 5 | 5 | 5 |
| 10 | 20 | 0 | 5 | 5 | 5 |
| | 10 | 0 | 5 | 5 | 5 |
| 11 | 20 | 0 | 4 | 5 | 5 |
| | 10 | 0 | 4 | 5 | 5 |
| 12 | 20 | 0 | 4 | 5 | 5 |
| | 10 | 0 | 4 | 5 | 5 |
| 13 | 20 | 0 | 4 | 5 | 5 |
| | 10 | 0 | 4 | 5 | 5 |
| 14 | 20 | 0 | 4 | 5 | 5 |
| | 10 | 0 | 4 | 5 | 5 |
| 15 | 20 | 0 | 5 | 5 | 5 |
| | 10 | 0 | 4 | 5 | 5 |
| 16 | 20 | 0 | 4 | 5 | 5 |
| | 10 | 0 | 4 | 5 | 5 |
| 17 | 20 | 0 | 4 | 5 | 5 |
| | 10 | 0 | 4 | 5 | 5 |
| 18 | 20 | 0 | 5 | 5 | 5 |
| | 10 | 0 | 4 | 5 | 5 |
| 19 | 20 | 0 | 4 | 5 | 5 |
| | 10 | 0 | 4 | 5 | 5 |
| 20 | 20 | 0 | 4 | 5 | 5 |
| | 10 | 0 | 4 | 5 | 5 |
| 21 | 40 | 0 | 4 | 5 | 5 |
| | 20 | 0 | 4 | 5 | 5 |
| 22 | 20 | 0 | 4 | 5 | 5 |
| | 10 | 0 | 4 | 5 | 5 |
| 23 | 40 | 0 | 4 | 5 | 5 |
| | 20 | 0 | 4 | 5 | 5 |
| 24 | 20 | 0 | 5 | 5 | 5 |
| | 10 | 0 | 4 | 5 | 5 |
| 26 | 20 | 0 | 4 | 5 | 5 |
| | 10 | 0 | 4 | 5 | 5 |
| 27 | 20 | 0 | 4 | 5 | 5 |
| | 10 | 0 | 4 | 5 | 5 |
| 28 | 20 | 0 | 4 | 5 | 5 |
| | 10 | 0 | 4 | 5 | 5 |
| 29 | 20 | 0 | 5 | 5 | 5 |
| | 10 | 0 | 3 | 5 | 5 |
| 30 | 20 | 0 | 4 | 5 | 5 |
| | 10 | 0 | 4 | 5 | 5 |
| 31 | 40 | 0 | 4 | 5 | 5 |
| | 20 | 0 | 4 | 5 | 5 |
| 32 | 20 | 0 | 5 | 5 | 5 |
| | 10 | 0 | 5 | 5 | 5 |

TABLE 1-continued

| Compound No. | Dosage (weight of active ingredient, g/are) | Rice plant | Barnyard grass | Broad-leaved weed | Nutsedge sp. |
|---|---|---|---|---|---|
| 33 | 20 | 0 | 4 | 5 | 5 |
|  | 10 | 0 | 4 | 5 | 5 |
| 34 | 20 | 0 | 4 | 5 | 5 |
|  | 10 | 0 | 4 | 5 | 5 |
| 35 | 20 | 0 | 5 | 5 | 5 |
|  | 10 | 0 | 5 | 5 | 5 |
| 36 | 20 | 0 | 4 | 5 | 5 |
|  | 10 | 0 | 4 | 5 | 5 |
| 37 | 20 | 0 | 4 | 5 | 5 |
|  | 10 | 0 | 4 | 5 | 5 |
| 39 | 20 | 0 | 4 | 5 | 5 |
|  | 10 | 0 | 4 | 5 | 5 |
| 40 | 20 | 0 | 4 | 5 | 5 |
|  | 10 | 0 | 4 | 5 | 5 |
| 41 | 20 | 0 | 5 | 5 | 5 |
|  | 10 | 0 | 4 | 5 | 5 |
| 42 | 20 | 0 | 4 | 5 | 5 |
|  | 10 | 0 | 4 | 5 | 5 |
| 43 | 20 | 0 | 5 | 5 | 5 |
|  | 10 | 0 | 5 | 5 | 5 |
| 44 | 20 | 0 | 4 | 5 | 5 |
|  | 10 | 0 | 4 | 5 | 5 |
| 45 | 20 | 0 | 4 | 5 | 5 |
|  | 10 | 0 | 4 | 5 | 5 |
| 46 | 20 | 0 | 5 | 5 | 5 |
|  | 10 | 0 | 4 | 5 | 5 |
| 47 | 20 | 0 | 5 | 5 | 5 |
|  | 10 | 0 | 4 | 5 | 5 |
| 48 | 20 | 0 | 5 | 5 | 5 |
|  | 10 | 0 | 5 | 5 | 5 |
| 49 | 20 | 0 | 5 | 5 | 5 |
|  | 10 | 0 | 4 | 5 | 5 |
| 50 | 20 | 0 | 5 | 5 | 5 |
|  | 10 | 0 | 5 | 5 | 5 |
| 51 | 20 | 0 | 5 | 5 | 5 |
|  | 10 | 0 | 5 | 5 | 5 |
| 52 | 20 | 0 | 4 | 5 | 5 |
|  | 10 | 0 | 4 | 5 | 5 |
| 53 | 40 | 0 | 4 | 5 | 5 |
|  | 20 | 0 | 4 | 5 | 5 |
| 54 | 20 | 0 | 5 | 5 | 5 |
|  | 10 | 0 | 5 | 5 | 5 |
| 57 | 40 | 0 | 4 | 5 | 5 |
|  | 20 | 0 | 4 | 5 | 5 |
| 58 | 20 | 0 | 5 | 5 | 5 |
|  | 10 | 0 | 4 | 5 | 5 |
| 59 | 20 | 0 | 5 | 5 | 5 |
|  | 10 | 0 | 4 | 5 | 5 |
| 60 | 20 | 0 | 5 | 5 | 5 |
|  | 10 | 0 | 5 | 5 | 5 |
| 61 | 20 | 0 | 5 | 5 | 5 |
|  | 10 | 0 | 4 | 5 | 5 |
| 62 | 20 | 0 | 5 | 5 | 5 |
|  | 10 | 0 | 5 | 5 | 5 |
| 63 | 20 | 0 | 5 | 5 | 5 |
|  | 10 | 0 | 5 | 5 | 5 |
| 64 | 20 | 0 | 4 | 5 | 5 |
|  | 10 | 0 | 4 | 5 | 5 |
| 65 | 20 | 0 | 5 | 5 | 5 |
|  | 10 | 0 | 5 | 5 | 5 |
| 66 | 20 | 0 | 5 | 5 | 5 |
|  | 10 | 0 | 4 | 5 | 5 |
| 67 | 20 | 0 | 5 | 5 | 5 |
|  | 10 | 0 | 4 | 5 | 5 |
| 69 | 20 | 0 | 4 | 5 | 5 |
|  | 10 | 0 | 4 | 5 | 5 |
| 70 | 20 | 0 | 4 | 5 | 5 |
|  | 10 | 0 | 4 | 5 | 5 |
| 73 | 40 | 0 | 4 | 5 | 5 |
|  | 20 | 0 | 4 | 5 | 5 |
| 74 | 40 | 0 | 4 | 5 | 5 |
|  | 20 | 0 | 4 | 5 | 5 |
| 75 | 20 | 0 | 5 | 5 | 5 |
|  | 10 | 0 | 4 | 5 | 5 |
| 78 | 40 | 0 | 4 | 5 | 5 |
|  | 20 | 0 | 4 | 5 | 4 |
| 79 | 20 | 0 | 4 | 5 | 5 |
|  | 10 | 0 | 4 | 5 | 5 |
| 80 | 20 | 0 | 5 | 5 | 5 |
|  | 10 | 0 | 4 | 5 | 5 |
| 81 | 20 | 0 | 5 | 5 | 5 |
|  | 10 | 0 | 4 | 5 | 5 |
| 82 | 20 | 0 | 5 | 5 | 5 |
|  | 10 | 0 | 4 | 5 | 5 |
| 83 | 20 | 0 | 4 | 5 | 5 |
|  | 10 | 0 | 4 | 5 | 5 |
| 84 | 20 | 0 | 5 | 5 | 5 |
|  | 10 | 0 | 4 | 5 | 5 |
| MCP | 20 | 3 | 4 | 5 | 5 |
|  | 10 | 2 | 3 | 5 | 5 |
| N'-(m-Benzyloxyphenyl)-N,N-dimethylurea | 20 | 1 | 2 | 5 | 4 |
|  | 10 | 0 | 2 | 5 | 4 |

EXAMPLE 12 (Post-emergence application test (weeds))

Plastic trays (35 cm×25 cm×10 cm (high)) were filled with upland field soil, and the seeds of redroot pigweed, common lambsquarters, radish, sunflower, cocklebur, annula morningglory, black nightshade, large crabgrass, barnyard grass and green foxtail were separately sowed in the trays and grown for 3 weeks in a green-house. The required amount of the test compound was sprayed to the foliage of the test plants over the top by means of a small hand sprayer. After the spraying, the test plants were grown for further 3 weeks in the green-house, and herbicidal activity was examined. The results are shown in Table 2. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, the weeds were in a 2- to 4-leaf stage and 2 to 12 cm in height although there was some difference depending upon the kind of weed.

TABLE 2

| Compound No. | Dosage (weight of active ingredient, g/are) | Redroot pigweed | Common lambsquarters | Radish | Sunflower | Cocklebur | Annual morningglory | Black nightshade | Large crabgrass | Barnyard grass | Green foxtail |
|---|---|---|---|---|---|---|---|---|---|---|---|
| 1 | 20 | 5 | 5 | 5 | 5 | 5 | 5 | 5 | 5 | 5 | 5 |
|  | 10 | 5 | 5 | 5 | 5 | 5 | 5 | 5 | 4 | 4 | 4 |
| 2 | 20 | 5 | 5 | 5 | 5 | 5 | 5 | 5 | 5 | 5 | 5 |
|  | 10 | 5 | 5 | 5 | 5 | 5 | 5 | 4 | 5 | 4 | 4 |
| 3 | 20 | 5 | 5 | 5 | 5 | 5 | 5 | 5 | 5 | 5 | 5 |
|  | 10 | 5 | 5 | 5 | 5 | 5 | 5 | 5 | 4 | 4 | 4 |

TABLE 2-continued

| Compound No. | Dosage (weight of active ingredient, g/are) | Herbicidal activity | | | | | | | | | |
|---|---|---|---|---|---|---|---|---|---|---|---|
| | | Redroot pigweed | Common lambs-quarters | Radish | Sunflower | Cock-lebur | Annual morning-glory | Black night-shade | Large crab-grass | Barnyard grass | Green foxtail |
| 4 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 5 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 5 |
| 6 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 7 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 8 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 9 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 10 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 11 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 13 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 14 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 15 | 20 | 5 | 5 | 5 | 5 | 5 | 5 | 5 | 5 | 4 | 5 |
| | 10 | 5 | 5 | 5 | 5 | 5 | 5 | 5 | 4 | 4 | 4 |
| 16 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 17 | 20 | 5 | 5 | 5 | 5 | 5 | 5 | 5 | 5 | 5 | 4 |
| | 10 | 5 | 5 | 5 | 5 | 5 | 5 | 5 | 4 | 4 | 4 |
| 18 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 20 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 22 | 20 | 5 | 5 | 5 | 5 | 5 | 5 | 5 | 4 | 5 | 4 |
| | 10 | 5 | 5 | 5 | 5 | 5 | 5 | 5 | 4 | 4 | 4 |
| 24 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 26 | 20 | 5 | 5 | 5 | 5 | 5 | 5 | 5 | 4 | 4 | 5 |
| | 10 | 5 | 5 | 5 | 5 | 5 | 5 | 5 | 4 | 4 | 4 |
| 27 | 20 | 5 | 5 | 5 | 5 | 5 | 5 | 5 | 4 | 5 | 4 |
| | 10 | 5 | 5 | 5 | 5 | 5 | 5 | 5 | 4 | 4 | 4 |
| 28 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 29 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 30 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 32 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 33 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 4 |
| 34 | 20 | 5 | 5 | 5 | 5 | 5 | 5 | 5 | 5 | 5 | 4 |
| | 10 | 5 | 5 | 5 | 5 | 5 | 5 | 5 | 4 | 5 | 4 |
| 35 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 36 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 4 |
| 37 | 20 | 5 | 5 | 5 | 5 | 5 | 5 | 5 | 5 | 5 | 4 |
| | 10 | 5 | 5 | 5 | 5 | 5 | 5 | 5 | 4 | 4 | 4 |
| 39 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 4 |
| 40 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 42 | 20 | 5 | 5 | 5 | 5 | 5 | 5 | 5 | 4 | 4 | 5 |
| | 10 | 5 | 5 | 5 | 5 | 5 | 5 | 5 | 4 | 3 | 3 |
| 43 | 20 | 5 | 5 | 5 | 5 | 5 | 5 | 4 | 4 | 4 | 5 |
| | 10 | 5 | 5 | 5 | 5 | 5 | 5 | 4 | | 4 | 4 |
| 44 | 40 | 5 | 5 | 5 | 5 | 5 | 5 | 5 | 5 | 4 | 4 |
| | 20 | 5 | 5 | 5 | 5 | 5 | 5 | 5 | 3 | 3 | 4 |
| 46 | 20 | 5 | 5 | 5 | 5 | 5 | 5 | 5 | 4 | 4 | 5 |
| | 10 | 5 | 5 | 5 | 5 | 5 | 5 | 5 | 3 | 4 | 3 |
| 47 | 20 | 5 | 5 | 5 | 5 | 5 | 5 | 4 | 4 | 4 | 4 |
| | 10 | 5 | 5 | 5 | 5 | 5 | 5 | 4 | 3 | 4 | 4 |
| 48 | 20 | 5 | 5 | 5 | 5 | 5 | 5 | 5 | 5 | 4 | 5 |
| | 10 | 5 | 5 | 5 | 5 | 5 | 5 | 5 | 3 | 4 | 4 |
| 50 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 51 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 5 |
| 52 | 40 | 5 | 5 | 5 | 5 | 5 | 5 | 5 | 4 | 5 | 5 |

TABLE 2-continued

| Compound No. | Dosage (weight of active ingredient, g/are) | Herbicidal activity | | | | | | | | | |
|---|---|---|---|---|---|---|---|---|---|---|---|
| | | Redroot pigweed | Common lambs-quarters | Radish | Sunflower | Cock-lebur | Annual morning-glory | Black night-shade | Large crab-grass | Barnyard grass | Green foxtail |
| | 20 | 5 | 5 | 5 | 5 | 5 | 5 | 5 | 4 | 3 | 3 |
| 56 | 20 | 5 | 5 | 5 | 5 | 5 | 5 | 5 | 4 | 4 | 4 |
| | 10 | 5 | 5 | 5 | 5 | 5 | 5 | 5 | 3 | 4 | 3 |
| 57 | 20 | 5 | 5 | 5 | 5 | 5 | 5 | 5 | 4 | 4 | 5 |
| | 10 | 5 | 5 | 5 | 5 | 5 | 4 | 4 | 3 | 3 | 3 |
| 58 | 20 | 5 | 5 | 5 | 5 | 5 | 5 | 5 | 5 | 4 | 5 |
| | 10 | 5 | 5 | 5 | 5 | 5 | 5 | 5 | 3 | 4 | 4 |
| 59 | 20 | 5 | 5 | 5 | 5 | 5 | 5 | 5 | 4 | 5 | 5 |
| | 10 | 5 | 5 | 5 | 5 | 5 | 5 | 5 | 4 | 3 | 3 |
| 60 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| 61 | 20 | 5 | 5 | 5 | 5 | 5 | 5 | 5 | 5 | 4 | 4 |
| | 10 | 5 | 5 | 5 | 5 | 5 | 5 | 5 | 3 | 4 | 3 |
| 62 | 20 | 5 | 5 | 5 | 5 | 5 | 5 | 5 | 4 | 5 | 4 |
| | 10 | 5 | 5 | 5 | 5 | 5 | 5 | 5 | 4 | 3 | 4 |
| 63 | 20 | 5 | 5 | 5 | 5 | 5 | 5 | 5 | 4 | 4 | 5 |
| | 10 | 5 | 5 | 5 | 5 | 5 | 5 | 5 | 4 | 3 | 4 |
| 64 | 20 | 5 | 5 | 5 | 5 | 5 | 5 | 5 | 4 | 4 | 5 |
| | 10 | 5 | 5 | 5 | 5 | 5 | 5 | 5 | 3 | 3 | 3 |
| 65 | 20 | 5 | 5 | 5 | 5 | 5 | 5 | 5 | 5 | 5 | 5 |
| | 10 | 5 | 5 | 5 | 5 | 5 | 5 | 5 | 3 | 4 | 4 |
| 66 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 3 |
| 67 | 20 | 5 | 5 | 5 | 5 | 5 | 5 | 5 | 4 | 4 | 4 |
| | 10 | 5 | 5 | 5 | 5 | 5 | 5 | 5 | 4 | 4 | 3 |
| 68 | 40 | 5 | 5 | 5 | 5 | 5 | 5 | 5 | 4 | 4 | 4 |
| | 20 | 5 | 5 | 5 | 5 | 5 | 5 | 5 | 3 | 3 | 4 |
| 70 | 20 | 5 | 5 | 5 | 5 | 5 | 5 | 5 | 5 | 4 | 5 |
| | 10 | 5 | 5 | 5 | 5 | 5 | 5 | 5 | 3 | 4 | 3 |
| 71 | 40 | 5 | 5 | 5 | 5 | 5 | 5 | 5 | 4 | 4 | 5 |
| | 20 | 5 | 5 | 5 | 5 | 5 | 5 | 5 | 3 | 3 | 5 |
| 75 | 20 | 5 | 5 | 5 | 5 | 5 | 5 | 5 | 4 | 5 | 5 |
| | 10 | 5 | 5 | 5 | 5 | 5 | 5 | 5 | 4 | 3 | 3 |
| 76 | 40 | 5 | 5 | 5 | 5 | 5 | 5 | 5 | 5 | 4 | 5 |
| | 20 | 5 | 5 | 5 | 5 | 5 | 5 | 5 | 3 | 3 | 3 |
| 77 | 40 | 5 | 5 | 5 | 5 | 5 | 5 | 5 | 4 | 5 | 4 |
| | 20 | 5 | 5 | 5 | 5 | 5 | 5 | 5 | 3 | 3 | 4 |
| 79 | 20 | 5 | 5 | 5 | 5 | 5 | 5 | 5 | 4 | 4 | 5 |
| | 10 | 5 | 5 | 5 | 5 | 5 | 5 | 5 | 3 | 4 | 3 |
| 80 | 20 | 5 | 5 | 5 | 5 | 5 | 5 | 5 | 4 | 4 | 4 |
| | 10 | 5 | 5 | 5 | 5 | 5 | 5 | 5 | 4 | 3 | 4 |
| 81 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 5 |
| 82 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 83 | 20 | 5 | 5 | 5 | 5 | 5 | 5 | 5 | 5 | 4 | 4 |
| | 10 | 5 | 5 | 5 | 5 | 5 | 5 | 5 | 3 | 3 | 4 |
| 84 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 3 |
| Chloro-xuron | 20 | 5 | 5 | 5 | 5 | 5 | 5 | 5 | 4 | 3 | 4 |
| | 10 | 5 | 5 | 5 | 5 | 5 | 5 | 5 | 2 | 3 | 3 |
| Bentazon | 20 | 3 | 5 | 5 | 5 | 5 | 4 | 5 | 1 | 2 | 0 |
| | 10 | 2 | 5 | 5 | 5 | 5 | 2 | 4 | 0 | 1 | 0 |
| N'-(m-Benzyl-oxyphenyl)-N,N-dimethyl-urea | 20 | 4 | 5 | 4 | 5 | 4 | 3 | 5 | 3 | 2 | 3 |
| | 10 | 4 | 5 | 4 | 5 | 3 | 1 | 4 | 1 | 2 | 2 |

EXAMPLE 13 (Post-emergence application test (cultivated plants))

Wagner's pots (1/5000 are) were each filled with upland field soil, and the seeds of soybean, cotton, sugar beet, corn, wheat and rice plant were sowed in the pots and grown for 3 weeks in a green-house. The required amount of the test compound was sprayed to the foliage of the test plants over the top by means of a small hand sprayer. After the spraying, the test plants were grown for further 3 weeks in the green-house, and phytotoxicity was examined. The results are shown in Table 3. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, soybean was in the second trifoliate stage, cotton in the 1-leaf stage, sugar beet in the 2-leaf stage, corn in the 2-leaf stage, wheat in the 2-leaf stage and rice plant in the 2-leaf stage.

TABLE 3

| Compound No. | Dosage (weight of active ingredient, g/are) | Phytotoxicity | | | | | |
|---|---|---|---|---|---|---|---|
| | | Soybean | Cotton | Sugar beet | Corn | Wheat | Rice plant |
| 1 | 20 | 1 | — | — | 1 | 1 | — |
| | 10 | 0 | — | — | 1 | 0 | — |
| 2 | 20 | 1 | — | — | — | 1 | — |
| | 10 | 0 | — | — | — | 1 | — |
| 3 | 20 | — | 1 | — | — | — | 1 |
| | 10 | — | 0 | — | — | — | 0 |
| 5 | 20 | 1 | — | — | — | — | 1 |
| | 10 | 1 | — | — | — | — | 1 |
| 10 | 20 | — | — | — | — | 1 | 1 |
| | 10 | — | — | — | — | 0 | 0 |
| 13 | 20 | 1 | — | — | — | 0 | 1 |
| | 10 | 1 | — | — | — | 0 | 0 |
| 16 | 20 | 1 | — | 1 | — | 1 | — |
| | 10 | 1 | — | 1 | — | 0 | — |
| 17 | 20 | 0 | 0 | — | 1 | 1 | 0 |
| | 10 | 0 | 0 | — | 1 | 0 | 0 |
| 18 | 20 | — | 1 | — | 1 | — | 0 |
| | 10 | — | 0 | — | 1 | — | 0 |
| 20 | 20 | 0 | — | — | 1 | — | 1 |
| | 10 | 0 | — | — | 0 | — | 0 |
| 24 | 20 | 0 | 1 | — | — | — | — |
| | 10 | 0 | 0 | — | — | — | — |
| 28 | 20 | 1 | 0 | — | — | — | 0 |
| | 10 | 0 | 0 | — | — | — | 0 |
| 29 | 20 | — | 1 | — | — | 1 | 0 |
| | 10 | — | 1 | — | — | 1 | 0 |
| 33 | 20 | 1 | — | — | 1 | 1 | 1 |
| | 10 | 1 | — | — | 1 | 1 | 0 |
| 35 | 20 | 1 | — | — | — | 1 | — |
| | 10 | 0 | — | — | — | 0 | — |
| 36 | 20 | 1 | 1 | — | — | 0 | — |
| | 10 | 0 | 0 | — | — | 0 | — |
| 40 | 20 | 1 | 1 | — | — | — | 0 |
| | 10 | 0 | 1 | — | — | — | 0 |
| 43 | 20 | 0 | — | — | 1 | — | 0 |
| | 10 | 0 | — | — | 1 | — | 0 |
| 48 | 20 | — | — | 0 | — | 0 | — |
| | 10 | — | — | 0 | — | 0 | — |
| 50 | 20 | 1 | 1 | — | — | 0 | — |
| | 10 | 0 | 0 | — | — | 0 | — |
| 58 | 20 | — | — | 1 | — | — | 0 |
| | 10 | — | — | 1 | — | — | 0 |
| 60 | 20 | — | — | — | 1 | — | — |
| | 10 | — | — | — | 0 | — | — |
| 61 | 20 | — | 1 | — | 1 | — | — |
| | 10 | — | 0 | — | 0 | — | — |
| 67 | 20 | 1 | — | — | — | — | 0 |
| | 10 | 0 | — | — | — | — | 0 |
| 70 | 20 | — | — | 1 | — | — | — |
| | 10 | — | — | 0 | — | — | — |
| 75 | 20 | 0 | — | — | — | — | 0 |
| | 10 | 0 | — | — | — | — | 0 |
| 79 | 20 | — | 0 | — | — | 0 | — |
| | 10 | — | 0 | — | — | 0 | — |
| 81 | 20 | 0 | 1 | — | — | 0 | — |
| | 10 | 0 | 0 | — | — | 0 | — |
| 82 | 20 | — | — | — | — | — | 0 |
| | 10 | — | — | — | — | — | 0 |
| 84 | 20 | 0 | — | — | — | — | — |
| | 10 | 0 | — | — | — | — | — |
| Chloroxuron | 20 | 2 | — | — | — | — | — |
| | 10 | 1 | — | — | — | — | — |
| Bentazon | 20 | 0 | — | — | 1 | — | 0 |
| | 10 | 0 | — | — | 0 | — | 0 |
| Fluometuron | 20 | — | 2 | — | — | — | — |
| | 10 | — | 1 | — | — | — | — |
| Atrazine | 20 | — | — | — | 1 | — | — |
| | 10 | — | — | — | 1 | — | — |
| Diuron | 20 | 5 | 5 | 5 | 5 | 5 | — |
| | 10 | 5 | 5 | 5 | 4 | 5 | — |

EXAMPLE 14 (Pre-emergence application test)

Plastic trays (35 cm×25 cm×10 cm (high) were filled with upland field soil, and the seeds of soybean, cotton, sugar beet, corn, wheat, rice plant, redroot pigweed, common lambsquarters, radish, common purslane and large crabgrass were sowed. The required amount of an emulsifiable concentrate was dispersed in water and sprayed at a volume of 5 liters per are to the whole surface of the soil by means of a small hand sprayer. After the spraying, the trays were placed in a green-house for 20 days, and phytotoxicity and herbicidal activity were examined. The results are shown in Table 4.

TABLE 4

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Sugar beet | Corn | Wheat | Rice plant | Redroot pigweed | Common lambsquarters | Radish | Common purslane | Large crabgrass |
| 2 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 4 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 6 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 9 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 5 | 4 |
| 18 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 5 | 4 |
| 20 | 40 | 0 | 0 | 0 | 0 | 0 | 0 | 5 | 5 | 5 | 5 | 4 |
| | 20 | 0 | 0 | 0 | 0 | 0 | 0 | 5 | 5 | 5 | 4 | |
| 29 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 32 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 35 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 42 | 80 | 0 | 0 | 0 | 0 | 0 | 0 | 5 | 5 | 5 | 5 | 4 |
| | 40 | 0 | 0 | 0 | 0 | 0 | 0 | 5 | 5 | 5 | 5 | 4 |
| 46 | 80 | 0 | 0 | 0 | 0 | 0 | 0 | 5 | 5 | 5 | 5 | 4 |
| | 40 | 0 | 0 | 0 | 0 | 0 | 0 | 5 | 5 | 5 | 5 | 4 |

TABLE 4-continued

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Sugar beet | Corn | Wheat | Rice plant | Redroot pigweed | Common lambs-quarters | Radish | Common purslane | Large crabgrass |
| 48 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 50 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 5 |
| 52 | 80 | 0 | 0 | 0 | 0 | 0 | 0 | 5 | 5 | 5 | 5 | 4 |
| | 40 | 0 | 0 | 0 | 0 | 0 | 0 | 5 | 5 | 5 | 5 | 4 |
| 55 | 80 | 0 | 0 | 0 | 0 | 0 | 0 | 5 | 5 | 5 | 5 | 5 |
| | 40 | 0 | 0 | 0 | 0 | 0 | 0 | 5 | 5 | 5 | 5 | 4 |
| 61 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 62 | 80 | 0 | 0 | 0 | 0 | 0 | 0 | 5 | 5 | 5 | 5 | 4 |
| | 40 | 0 | 0 | 0 | 0 | 0 | 0 | 5 | 5 | 5 | 5 | 4 |
| 72 | 80 | 0 | 0 | 0 | 0 | 0 | 0 | 5 | 5 | 5 | 5 | 5 |
| | 40 | 0 | 0 | 0 | 0 | 0 | 0 | 5 | 5 | 5 | 5 | 4 |
| 75 | 80 | 0 | 0 | 0 | 0 | 0 | 0 | 5 | 5 | 5 | 5 | 4 |
| | 40 | 0 | 0 | 0 | 0 | 0 | 0 | 5 | 5 | 5 | 5 | 4 |
| 80 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| 81 | 40 | 0 | 0 | 0 | 0 | 0 | 0 | 5 | 5 | 5 | 5 | 5 |
| | 20 | 0 | 0 | 0 | 0 | 0 | 0 | 5 | 5 | 5 | 5 | 4 |
| Chloramben | 20 | 0 | 4 | — | 3 | 1 | — | 2 | 2 | 0 | 5 | 3 |
| | 10 | 0 | 3 | — | 2 | 0 | — | 2 | 1 | 0 | 5 | 2 |
| Diuron | 20 | 5 | 3 | — | 4 | 5 | — | 5 | 5 | 5 | 5 | 4 |
| | 10 | 4 | 1 | — | 2 | 4 | — | 5 | 5 | 5 | 5 | 3 |

The application of the compounds (I) as fungicides will be illustrated in the following Example wherein a commercially available fungicide known under the generic name "triforine" and having the following formula was used for comparison:

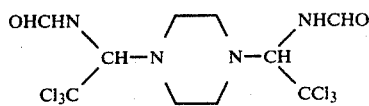

EXAMPLE 15 (Protective effect on leaf rust of wheat)

Plastic pots (150 ml volume) were filled with sandy soil, and 10 to 15 seeds of wheat (var.: Nohrin No. 51) were sowed and grown up to the one-leaf stage in an air-controlled room kept at a temperature of 18° to 23° C. for 7 days. The wheats were inoculated with *Puccinia recondita* and placed in a humid chamber for 16 hours. Then, each of the emulsifiable concentrates containing the test compounds was diluted with water and sprayed on the test plants at a rate of 15 ml/pot. The test plants were placed in a chamber kept at 23° C. and grown under a fluorescent lamp for additional 10 days. The degree of infection at the one-leaf stage was examined by the following method: the leaves examined were measured for a percentage of infected area and classified into the corresponding disease indices, 0, 0.5, 1, 2 and 4. The disease severity was calculated according to the following equation:

| Disease index | Infection state |
|---|---|
| 0 | No infected surface area |
| 0.5 | Infected surface area of less than 5% |
| 1 | Infected surface area of less than 20% |
| 2 | Infected surface area of less than 50% |
| 4 | Infected surface area of more than 50% |

$$\text{Disease severity (\%)} = \frac{\Sigma(\text{Disease index}) \times (\text{Number of leaves})}{4 \times (\text{Total number of leaves examined})} \times 100$$

The prevention value was calculated according to the following equation:

$$\text{Prevention value (\%)} = 100 - \frac{\text{Disease severity in treated pots}}{\text{Disease severity in untreated pots}}$$

The results are shown in Table 5, from which it is understood that the compounds (I) of the present invention exhibit a pronounced protective effect against leaf rust of wheat.

TABLE 5

| Compound No. | Concentration of active ingredient (ppm) | Prevention value (%) |
|---|---|---|
| 1 | 500 | 100 |
| 2 | 500 | 100 |
| 5 | 500 | 100 |
| 16 | 500 | 100 |
| 23 | 500 | 90 |
| 28 | 500 | 95 |
| 39 | 500 | 100 |
| 42 | 500 | 100 |
| 43 | 500 | 100 |
| 50 | 500 | 99 |
| Triforine | 500 | 82 |

What is claimed is:
1. A compound of the formula:

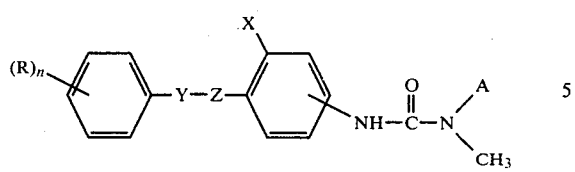

wherein A is a hydrogen atom, a methyl group or a methoxy group, R is the same or different and is a halogen atom, a lower alkyl group, a lower alkoxy group, a lower alkylthio group, a trifluoromethyl group, a cyano group or a methylenedioxy group, X is a hydrogen atom or a halogen atom, Y is an oxygen atom or a sulfur atom, Z is a lower alkylene group and n is an integer of 0 to 3, provided that the substituted ureido group is present at the m- or p-position with respect to the substituent represented by the symbol X and at the same time at the m- or p-position with respect to the substituent represented by the symbol Z.

2. The compound according to claim 1, wherein the substituted ureido group is present at the m-position with respect to the substituent represented by the symbol X and at the same time at the p-position with respect to the substituent represented by the symbol Z.

3. The compound according to claim 1, wherein the substituted ureido group is present at the p-position with respect to the substituent represented by the symbol X and at the same time at the m-position with respect to the substituent represented by the symbol Z.

4. The compound according to claim 3, wherein A is a methyl group or a methoxy group, X is a hydrogen atom, Y is an oxygen atom and Z is a methylene group.

5. The compound according to claim 3, wherein A is a methyl group or a methoxy group, X is a hydrogen atom, Y is an oxygen atom and Z is a 1-methyltrimethylene group (—CH(CH₃)CH₂CH₂—).

6. The compound according to claim 3, wherein A is a methyl group or a methoxy group, R is a trifluoromethyl group at the m-position with respect to the substituent represented by the symbol Y, X is a hydrogen atom, Y is an oxygen atom, Z is a methylene group and n is 1.

7. The compound according to claim 3, wherein A is a methyl group or a methoxy group, R is a chlorine atom at the m-position with respect to the substituent represented by the symbol Y, X is a hydrogen atom, Y is an oxygen atom, Z is a methylene group and n is 1.

8. The compound according to claim 3, wherein A is a methyl group or a methoxy group, R is a chlorine atom at the m- or p-position with respect to the substituent represented by the symbol Y, X is a hydrogen atom, Y is an oxygen atom, Z is a methylene group and n is 2.

9. The compound according to claim 3, wherein A is a methyl group or a methoxy group, R is a hydrogen atom, X is a hydrogen atom, Y is an oxygen atom, Z is a 1-methyl-trimethylene group (—CH(CH₃)CH₂CH₂—) and n is 1.

10. A herbicidal and/or fungicidal composition which comprises as an active ingredient at least one compound having the formula:

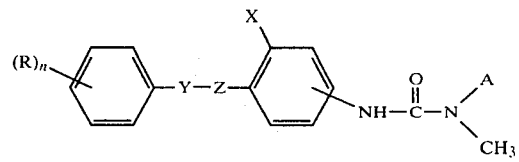

wherein A is a hydrogen atom, a methyl group or a methoxy group, R is the same or different and is a halogen atom, a lower alkyl group, a lower alkoxy group, a lower alkylthio group, a trifluoromethyl group, a cyano group or a methylenedioxy group, X is a hydrogen atom or a halogen atom, Y is an oxygen atom or a sulfur atom, Z is a lower alkylene group and n is an integer of 0 to 3, provided that the substituted ureido group is present at the m- or p-position with respect to the substituent represented by the symbol X and at the same time at the m- or p-position with respect to the substituent represented by the symbol Z, and an inert carrier.

11. The composition according to claim 10, wherein the concentration of the active ingredient is from about 1 to 100% by weight.

12. A herbicidal and/or fungicidal composition as defined in claim 10 wherein the substituted ureido group is present at the m-position with respect to the substituent represented by the symbol X and at the same time at the p-position with respect to the substituent represented by the symbol Z.

13. A herbicidal and/or fungicidal composition as defined in claim 10, wherein the substituted ureido group is present at the p-position with respect to the substituent represented by the symbol X and at the same time at the m-position with respect to the substituent represented by the symbol 2.

14. A method for controlling weeds and/or fungi, which comprises contacting the weeds and/or fungi with an effective herbicidal or fungicidal amount of at least one of the compounds according to claim 1.

15. A method for selectively combating weeds and/or fungi in the cultivation of soybean and/or gramineous crops, which comprises applying a herbicidally and/or fungicidally effective amount of at least one of the compounds according to claim 1 to the area wherein the soybean and/or gramineous crops are cultivated.

16. A method of selectively combating weeds and/or fungi in the cultivation of gramineous crops, which comprises applying a herbicidally and/or fungicidally effective amount of at least one of the compounds according to claim 1 to the area wherein the gramineous crops are cultivated.

17. A method according to claim 14, 15, or 16 wherein the compounds are used as a herbicide and are applied in an amount of 2 to 200 grams of the active ingredient per are.

18. A method according to claim 14, 15, or 16 wherein the compounds are used as fungicides and are applied in an amount of from 0.2 to 50 grams of the active ingredient per are.

* * * * *